(12) United States Patent
Deisboeck et al.

(10) Patent No.: US 6,602,701 B2
(45) Date of Patent: Aug. 5, 2003

(54) THREE-DIMENSIONAL CELL GROWTH ASSAY

(75) Inventors: Thomas S. Deisboeck, Boston, MA (US); E. Antonio Chiocca, Wakefield, MA (US); John D. Wright, Sandown, NH (US)

(73) Assignee: The General Hospital Corporation, Boston, MA (US)

( * ) Notice: Subject to any disclaimer, the term of this patent is extended or adjusted under 35 U.S.C. 154(b) by 7 days.

(21) Appl. No.: 09/758,644

(22) Filed: Jan. 11, 2001

(65) Prior Publication Data

US 2001/0031480 A1 Oct. 18, 2001

Related U.S. Application Data

(60) Provisional application No. 60/175,616, filed on Jan. 11, 2000.

(51) Int. Cl.[7] .............................................. C12M 3/00
(52) U.S. Cl. ............................... 435/288.2; 435/304.2; 422/102
(58) Field of Search ......................... 435/288.2, 297.5, 435/304.2, 304.3; 422/102; 220/502; 604/89

(56) References Cited

U.S. PATENT DOCUMENTS

| | | | | |
|---|---|---|---|---|
| 3,052,346 A | * | 9/1962 | Maron | 220/502 |
| 3,470,929 A | * | 10/1969 | Thornton | 220/502 |
| 4,721,393 A | * | 1/1988 | Kwast | 220/502 |
| 5,482,854 A | * | 1/1996 | O'Leary et al. | 215/229 |
| 6,001,643 A | * | 12/1999 | Spaulding | 435/288.2 |

OTHER PUBLICATIONS

Jörgen Carlsson, "A Proliferation Gradient in Three–Dimensional Colonies of Cultured Human Glioma Cells," Int. J. Cancer, 20:129–136, 1977.
Giese et al., "Substrates for Astrocytoma Invasion," Neurosurgery, 37(2):294–302, 1995.
Khoshyomn et al., "Four–dimensional analysis of human brain tumor spheroid invasion into fetal rat brain aggregates using confocal scanning laser microscopy," J. of Neuro-Oncology, 38:1–10, 1998.
Lillian A. Repesh, "A New in vitro Assay for Quantitating Tumor Cell Invasion," Invasion Metastasis, 9:192–208, 1989.

* cited by examiner

*Primary Examiner*—William H. Beisner
(74) *Attorney, Agent, or Firm*—Fish & Richardson P.C.

(57) ABSTRACT

The invention relates to devices and methods for growing cells in vitro in an enclosed device that allows for a three-dimensional measurement over time of both their proliferative and/or invasive properties. By growing the cells in an enclosed matrix that resembles the environment that the cells confront in vivo, the cells can divide, invade, and form branched networks as they do in living tissue, e.g., in an individual. The devices of the invention include a test chamber in which cells, e.g., tumor cells, are placed and permitted to divide and/or invade. Cells can be placed within an insert within a chamber of the device. A delivery chamber that connects to the test chamber enables the delivery of agents that can be studied, e.g., for their therapeutic potential. The assay devices of the invention can be used as model systems to study cancer biology and to evaluate the efficacy of anti-cancer therapeutics.

18 Claims, 8 Drawing Sheets

THREE-DIMENSIONAL CELL GROWTH ASSAY

CROSS-REFERENCE TO RELATED APPLICATIONS

This application claims priority from U.S. Provisional Application No. 60/175,616, filed Jan. 11, 2000, which is incorporated herein by reference in its entirety.

STATEMENT AS TO FEDERALLY-SPONSORED RESEARCH

This invention was made with Government support under NIH/NCI R21CA84509-01 awarded by the National Institutes of Health. The Government has certain rights in the invention.

FIELD OF THE INVENTION

The invention relates to devices and methods for analyzing cellular growth in vitro.

BACKGROUND OF THE INVENTION

Tumors grow through two primary processes: proliferation and invasion. Proliferative growth represents the increase in size of the central tumor mass through the division of cells. Invasive growth occurs in tissues in the regions adjacent to and around the central tumor mass. In the invasion process, individual tumor cells detach from the central tumor mass and begin to actively move through the surrounding, non-tumorous tissue, either by compression or enzymatic degradation. The presumably highly branched cells formed by these invading cells represent a dynamically evolving network pattern. The chains formed in the invasive network can be as thin as a single cell in width. Further, the invading cells are significantly elongated along the direction in which they are traveling.

Malignant tumors such as highly malignant brain tumors (e.g., gliomas and glioblastoma multiform) have several features such as proliferation, invasion, central necrosis/apoptosis and neo-vascularization. Tumors outside the central nervous system show extensive metastasis by way of the blood circulatory and lymphatic systems.

Several in vitro assays have been described that are designed to measure either cell proliferation, migration, or invasion. For example, a cell colony/spheroid-agarose assay uses cell suspensions within, or multicellular tumor spheroids placed on top of agarose (in a cell culture dish), which is then covered with cell culture medium. Carlsson J., *Int. J. Cancer*, 20:129–136, 1977. The assay is designed to study the growth dynamics of the cell colonies or spheroid. The medium superlayer distributes growth factors and growth limiting factors produced by the tumor, without preserving their important regional concentration differences (i.e., higher concentration around the tumor). Also, the superlayer has to be changed routinely, altering the environmental setting.

A 2D migration assay can be used to describe the movement of a cell population from a central area in an expanding circle. Giese A., *Neurosurgery*, 37:294–302, 1995. The cells are placed in a cell culture dish and covered with medium. Aside from the edge of the dish, there is no mechanical confinement and no chemo-gradients can be established due to "equalizing" in the medium superlayer.

Invasiveness assays (e.g., commercially available through Costar® as the 24-well Transwell™ System) use a medium-supplemented, two-chamber system, which is designed to detect cell migration between the two chambers. Repesh L. A., *Invasion Metastasis*, 9:192–208, 1989. The insert (top chamber) has a polycarbonate membrane on the bottom, which has a number of pores (8 µm size). After a certain number of cells are placed onto this membrane, they start to move through the pores and drop into the lower chamber where they either start anchorage-independent growth or eventually attach. After an observation period the cell number in both chambers is counted (Coulter Counter System®) and a ratio indicates the specific invasive potential of the cell line used. A variation of the assay uses a Matrigel® layer on top of the polycarbonate membrane to investigate the enzymatic activity of the cells to digest their way towards the pores.

A spheroid-fetal rat brain aggregate assay uses rat brain aggregates co-cultured on a medium/agar-layer and covered with a cell-culture medium that is changed routinely. Khoshyomn S., *J. Neuro-Oncology*, 38:1–10, 1998. The migration capacity of the tumor cells is determined by the destruction of the rat brain aggregate, not by the direct measurement of cell branches.

SUMMARY OF THE INVENTION

The invention is based on the discovery that cells can be grown in vitro in an enclosed device that allows for a three-dimensional measurement of both their proliferative and invasive properties. By growing the cells in an enclosed matrix that resembles the environment the cells confront in vivo, the cells can divide, invade, and form branched networks as they are thought to do in living tissue, e.g., in an individual. Propagating the cells in vitro in this manner allows for the imaging and temporal-spatial analysis of cells and cellular behavior that cannot be easily achieved when the cells are grown inside an organism. The methods and devices of the invention are particularly useful for studying the growth of tumor cells in vitro. The assay devices of the invention can thus be used as model systems to study cancer biology and to evaluate the efficacy of anti-cancer therapeutics.

In general, the invention features an assay device for measuring the proliferation and/or invasion of cells, e.g., tumor cells. The device includes a test chamber and a first delivery chamber arranged to contact the test chamber. The device can also include a control chamber, e.g., arranged to contact the first delivery chamber or a second delivery chamber. The first delivery chamber includes a wall with an opening to enable fluid communication between the first delivery chamber and the test chamber. The device also includes a hollow cylinder enclosing a lumen and arranged within the first delivery chamber, the cylinder including a wall with a hole that can be aligned with the opening in the first delivery chamber wall to enable fluid communication between the cylinder lumen and the test chamber.

The assay device can further include a cover that sealingly contacts the delivery chamber, the test chamber, and the control chamber, if present. The assay device can also include a moveable interior wall that is arranged within the test chamber to be moved laterally within the test chamber, e.g., by turning screws located in holes in an outer wall of the test chamber. The assay device optionally includes a second moveable interior wall that is arranged within the control chamber to be moved laterally within the control chamber, e.g., by turning screws located in holes in an outer wall of the control chamber.

The invention also features an assay device that includes a plurality of cylinders, each having a hole that can be aligned with the opening in the delivery chamber wall to enable fluid communication between the cylinder and the test chamber, wherein the cylinders are interchangeable and each has a hole of a different size. In addition, the assay device can also include a second delivery chamber arranged to contact the control chamber, e.g., in the same manner that the first delivery chamber is arranged to contact the test chamber. This would allow the control chamber to be exposed to a control fluid, as compared to a test fluid in the test chamber. The control chamber can include a moveable wall that is arranged to move within the control chamber.

The test chamber of an assay device can include an outer wall with an opening to enable fluid communication between the test chamber and the exterior of the assay device. An assay device can also include a hollow insert constructed to fit within the test chamber. The hollow insert can contain a moveable wall that is arranged to move within the insert.

In another embodiment, the invention features an assay system for measuring the proliferation and/or invasion of cells. The assay system includes an assay device of the invention, a pump having an input and an output, a first conduit that connects one end of the cylinder to the pump input, and a second conduit that connects a second end of the cylinder to the pump output to permit flow of fluid, e.g., a liquid or gas, from the pump, through the cylinder in the delivery chamber of the device, and back to the pump.

The assay system can also include an injection port connected to a conduit that permits the introduction of substances into the system, e.g., by microinjection. Additionally, the assay system can include a device of the invention that includes a first moveable interior wall that is arranged within the test chamber to be moved laterally within the test chamber, e.g., by turning screws located in holes in an outer wall of the test chamber. Furthermore, the assay system can include a device of the invention including a second moveable interior wall that is arranged within a control chamber to be moved laterally within the control chamber, e.g., by turning screws located in holes in an outer wall of the control chamber. The advancement of the walls allows for a continuous controlled increase of the mechanical confinement within the chambers and the study of its structural and functional impact on the distinct features of the cell system (e.g., proliferation and/or invasion).

The test chamber of an assay device of an assay system can include an outer wall with an opening to enable fluid communication between the test chamber and the exterior of the assay device. An assay system can also include a hollow insert constructed to fit within the test chamber. The hollow insert can contain a moveable wall that is arranged to move within the insert.

In another aspect, the invention features a method for detecting the proliferation of cells, e.g., tumor cells. This method includes the following steps: (1) placing one or more cells in a matrix within the test chamber of a device of the invention; (2) placing the device under conditions that permit the growth of the cells contained therein; (3) aligning the hole in the wall of the cylinder and the opening in the wall of the first delivery chamber to enable liquid medium to flow into the test chamber; (4) flowing liquid medium through the cylinder within the delivery chamber of the device; and (5) evaluating the proliferation of the cells within both the test chamber. The test chamber can include a moveable wall and the method can include moving the moveable wall. In one example, the placing of the one or more cells in a matrix within the test chamber includes placing the one or more cells within a matrix in a hollow insert, and placing the hollow insert within the test chamber. The insert can include a moveable wall and the method can include moving the moveable wall.

The method can also include flowing a gas through the cylinder within the delivery chamber of a device of the invention. The method can evaluate the proliferation of the tumor cells by counting the numbers of cells within the control and test chambers, e.g., by microscopic analysis of cells within the device. The tumor cells can optionally be extracted from the device for analysis.

The invention also features methods for detecting the proliferation of tumor cells wherein therapeutic agents are in the liquid medium that flows into the test chamber of the device. Additionally, according to the methods of the invention, therapeutic agents can be delivered to the test chamber of the device through holes in an outer wall of the test chamber. The methods also include the step of flowing liquid medium from the test chamber through a hole in the outer wall of the test chamber to the exterior of the device.

In another embodiment, the invention features a method for detecting invasion of tumor cells. The method includes the following steps: (1) placing tumor cells in a matrix within both the test chamber of a device of the invention; (2) placing the device under conditions that permit the invasion of the cells contained therein; (3) aligning the hole in the wall of the cylinder and the opening in the wall of the delivery chamber to enable liquid medium to flow into the test chamber; (4) flowing liquid medium through the cylinder within the delivery chamber of the device; and (5) evaluating invasion of the cells within the test chamber. The method also includes flowing a gas through the cylinder within the delivery chamber of the device. The method can evaluate the invasion of tumor cells by microscopic analysis of cells within the device. The tumor cells can be extracted from the device for analysis as part of the method.

The invention also features methods for detecting invasion of tumor cells, wherein therapeutic agents are included in the liquid medium that flows into the test chamber of the device. Additionally, according to the methods of the invention, therapeutic agents can be delivered to the test chamber of the device through holes in an outer wall of the test chamber.

The assay devices of the invention allow for dynamic three-dimensional measurements of the proliferation and invasion of multicellular systems such as tumor cells in an in vitro assay. The lack of a medium superlayer allows for some of the devices to be tilted to any angle and even flipped 180 degrees for true three-dimensional measurement, without an alteration of the internal environment. The new assay devices of the invention have the advantage of being able to investigate tumors as multi-featured systems.

The invention also provides advantages over in vivo assays. Single cell invasion cannot be easily studied in situ or in vivo (e.g., in animal models) because of the limitations of the resolution threshold of imaging methods. The new assays allow for in vitro growth of cells, e.g., tumor cells, in three dimensions over time so as to mimic tumor growth in vivo, but also render the cells accessible to a wide range of in vitro techniques that allow the study of their biology and their reaction to various agents, including potential therapeutics. The new assay systems allow for a continuous flow through gel-embedded cells and thus allows for repeated measurements of cells as they grow in a three-dimensional environment. The devices described herein allow for easier focusing on a tumor using microscopic techniques, thus increasing the ability to achieve sharp pictures from all angles. The advanced, new in vitro models also limit the amount of necessary in vivo experimentation by providing a pre-evaluation and a focus on promising drugs.

Unless otherwise defined, all technical and scientific terms used herein have the same meaning as commonly understood by those of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In case of a conflict in terminology, the present specification will control. In addition, the described materials and methods are illustrative only and are not intended to be limiting.

Other features and advantages of the invention will be apparent from the following detailed description and the claims.

DETAILED DESCRIPTION

The invention relates to devices and methods for growing cells in vitro in an enclosed device that allows for a three-dimensional measurement over time of both their proliferative and invasive properties. By growing the cells, e.g., tumor cells, in an enclosed matrix that resembles the environment that the cells confront in vivo, the cells can divide, invade, and form branched networks as they are thought to in living tissue, e.g., in an animal or a human. Propagating the cells in vitro in this manner allows for an analysis of cells, e.g., tumor cells, as multi-featured systems and promotes the development of computational models based on experimental data. Devices described herein can be used for short term or long term experiments.

A central feature of the devices of the invention is that they include a test chamber in which cells are placed and permitted to divide and invade. The devices of the invention can also include a control chamber. A delivery chamber that connects to the test chamber allows for the delivery of agents that can be studied for their therapeutic potential. The assay devices of the invention can thus be used as model systems to study multicellular biological systems. For example, they can be used to study cancer biology and to evaluate the efficacy of anti-cancer therapeutics.

Construction of the Assay Device

Figure 1:
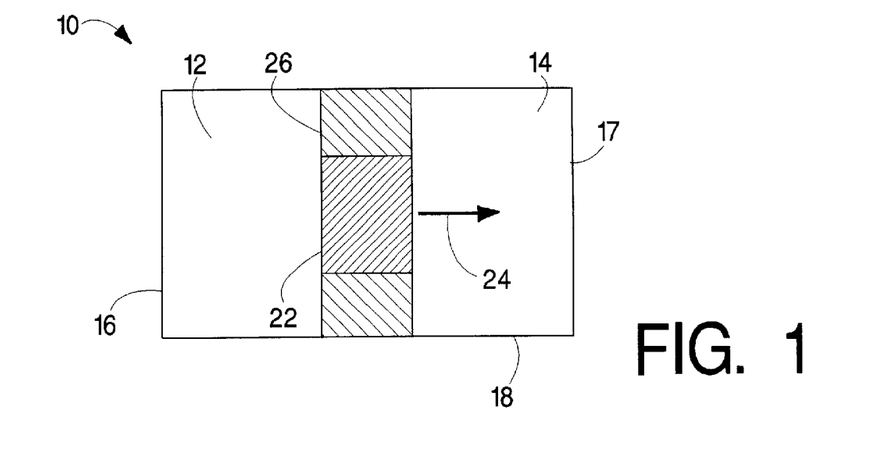
FIG. 1 is a schematic representation (top view) of a three-chambered assay device of the invention.

A top view of a device 10 of the invention is shown in FIG. 1. This device has a first side wall 16, e.g., of about 8 to 10 mm in length, and a second side wall 18, e.g., of about 12 to 30 mm in length. The device in the examples below is rectangular, but can be square, round, elliptical, or other overall shape, given that other dimensions of device components are adjusted to conform to the device shape. The walls of device 10 can be made of plexiglass, glass, or others material of similar rigidity and transparency. Device 10 is divided into three chambers, a test chamber 14, a control chamber 12, and a delivery chamber 26, that can be arranged centrally to separate the other two chambers. The test chamber 14 is treated experimentally in assays performed using the device and the control chamber 12 is left untreated. By having a system with two tumor-containing chambers, one can set up both experimental and control assays at the same time using the same lots of tumor cells, gel, and media, and thus limit the effect of slightly different growth factor compositions and facilitating the set-up for both experiments.

Figure 2A:
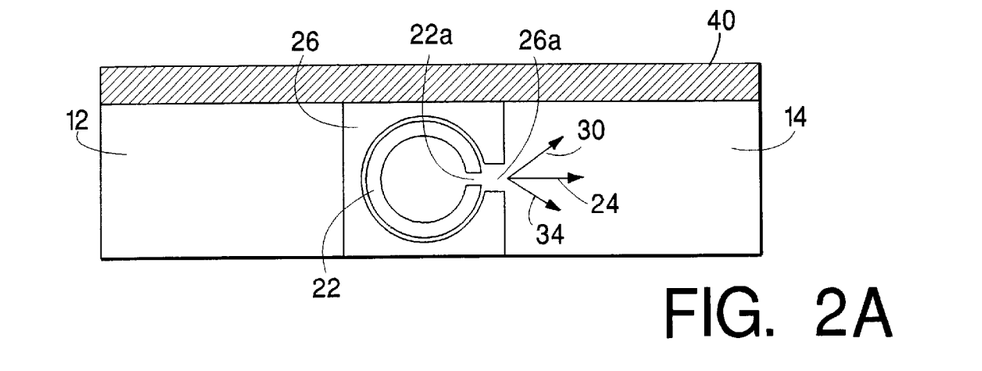
FIG. 2a is a cross-sectional view of the delivery chamber and the cylinder of a device of the invention, in which a substance is permitted to flow from the cylinder into the test chamber.
Figure 2B:
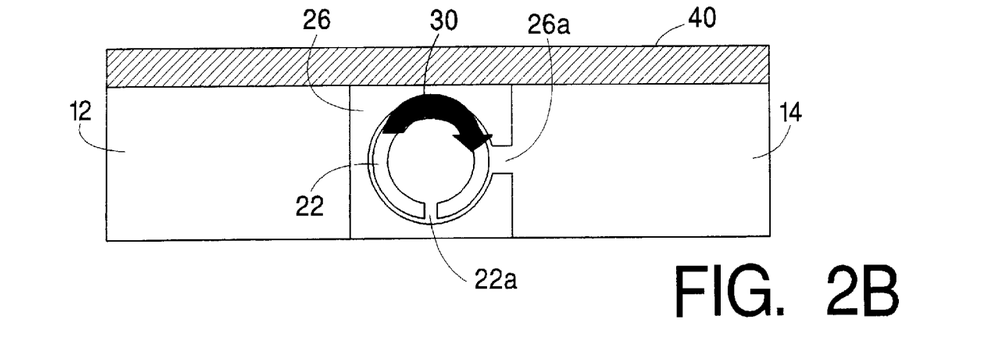
FIG. 2b is a cross-sectional view of the delivery chamber and the cylinder of a device of the invention, in which the cylinder has been rotated to prevent flow from inside the cylinder into the test chamber.

Delivery chamber 26 is shown in FIG. 1 to extend from one side of the device to the other, contacting both the top and the bottom of the device 10. In FIG. 1, delivery chamber 26 separates the other two chambers 12 and 14, but can be arranged on either side of test chamber 14. The only requirement is that delivery chamber 26 contacts the test chamber 14, to enable flow of liquids inside the delivery chamber into the test chamber. If delivery chamber 26 is located for example on side wall 17 of device 10, then a wall would be required to separate test chamber 14 from control chamber 12. As shown in FIGS. 2a and 2b, a hollow cylinder 22 can be located within delivery chamber 26. Cylinder 22 can be round and can be made of plastic. Delivery chamber 26 has a hole 26a in the wall (or walls) located between it and the test chamber 14. Similarly, cylinder 22 has a hole 22a located in its wall that corresponds in location to hole 26a in the delivery chamber 26. These holes are arranged to permit the flow (arrow 24 in FIGS. 1 and 2a) of a substance into test chamber 14. Only when both holes 22a and 26a are aligned will the substance flow into the test chamber 14.

The size of hole 26a in delivery chamber 26 is larger than that of hole 22a in cylinder 22 and can be customized. Cylinder 22 can be removed, for example with a miniature screwdriver, to customize the size of its hole. Thus, any desired changes in hole size, and thus flow rate and volume delivered into the test chamber 14, can be achieved by modifying cylinder 22. Additionally, a collection of cylinders 22 can be provided that each have holes of different sizes, thus permitting an immediate selection of the appropriate hole size for different assays without the need for any mechanical modifications to the rest of the device. The cylinder 22 can optionally be operated from the top of the device by removing the top of the device and aligning hole 26a and 22a, from the outside, without having to unhook the connectors and/or tubes.

FIGS. 2a and 2b illustrate the rotation of cylinder 22 to control flow of material into the test chamber 14. In FIG. 2a, the lumen inside delivery chamber 26 contains cylinder 22. This cylinder 22 can be rotated inside delivery chamber 26, and can be entirely removed. When put in place, cylinder 22 can be connected to the outside conduits and pump mechanism. As illustrated in FIG. 2a, when holes 26a and 22a are lined up with each other, fluid can flow into the test chamber 14. Because hole 26a of delivery chamber 26 is larger than hole 22a of cylinder 22, liquids can be made to flow into test chamber 14 at various angles (arrows 24, 30, and 34) based upon the degree of lineup between the two holes. FIG. 2b illustrates the further rotation (arrow 30) of cylinder 22 such that hole 26a and hole 22a are no longer aligned. This prevents the flow of substances from inside cylinder 22 into test chamber 14. In addition to fluids, the assay system can also be arranged to deliver a gas to test chamber 14 when the holes in delivery chamber 26 and cylinder 22 are aligned. For example, various concentrations of $O_2$ and $CO_2$ can be used to evaluate the dependence of partial pressure on the cell system. Additionally, the assay system can be constructed to deliver a fluid and gas combination, e.g. to mimic the conditions present in normal blood flow.

In addition to the flow of substances into test chamber 14, the device 10 can also be constructed to deliver substances (e.g., fluid or gas) to control chamber 12. This can be accomplished in the same manner as for delivery to test chamber 14, e.g., by providing a delivery chamber and optionally a cylinder having holes that may be aligned to permit flow into the control chamber 12. If the substances to be delivered to control chamber 12 and test chamber 14 differ, then separate input and output conduits and pumping systems can be arranged for two separate delivery chamber and cylinder combinations that each connect to only a single chamber, thereby preventing the cross-flow of substances intended to be delivered to a single chamber.

Figure 3A:
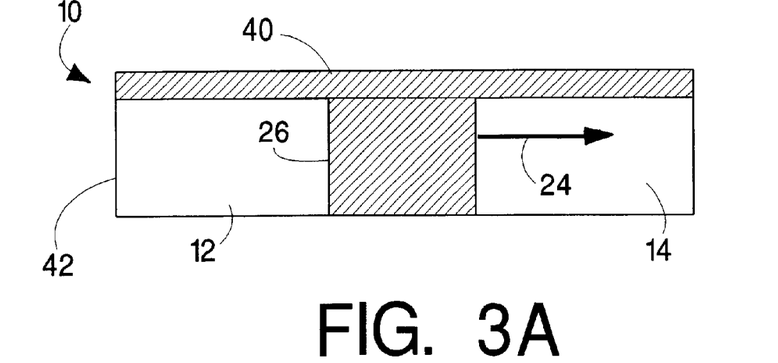
FIG. 3a is a schematic representation (side view) of a three-chambered device of the invention with a cover in place.

As illustrated in the side view of the device 10 in FIG. 3a, a cover 40 is placed on top of the device so as to fit tightly and seal the device. A sealant, e.g., silicon glue, can be used to attach the cover to the device. Preferably, the sealant can easily be removed and thus permits the reuse of the device. As shown in this side view, side walls 42 of the device can have a height of about 4 to 10 mm. Because the device can have a tight fitting cover 40, and has no air holes, the possibility of contamination of the cells growing inside the device is relatively small. The addition of antibiotics to the gel/medium mixture also functions to minimize the possibility of contamination. The mechanism for attaching the cover 40 is further described in the side view of FIG. 3b. A ridge 50 extends above the top of three of the walls of the device. The top of ridge 50 has an overhang 52 that receives an edge of the cover 40 and holds it tightly in place. This ridge 50 functions essentially like a frame. By extending above three of the four side walls of the device, ridge 50 permits cover 40 to slide in place to provide a tight fit between cover 40 and device 10.

Moveable Interior Wall

Figure 4:
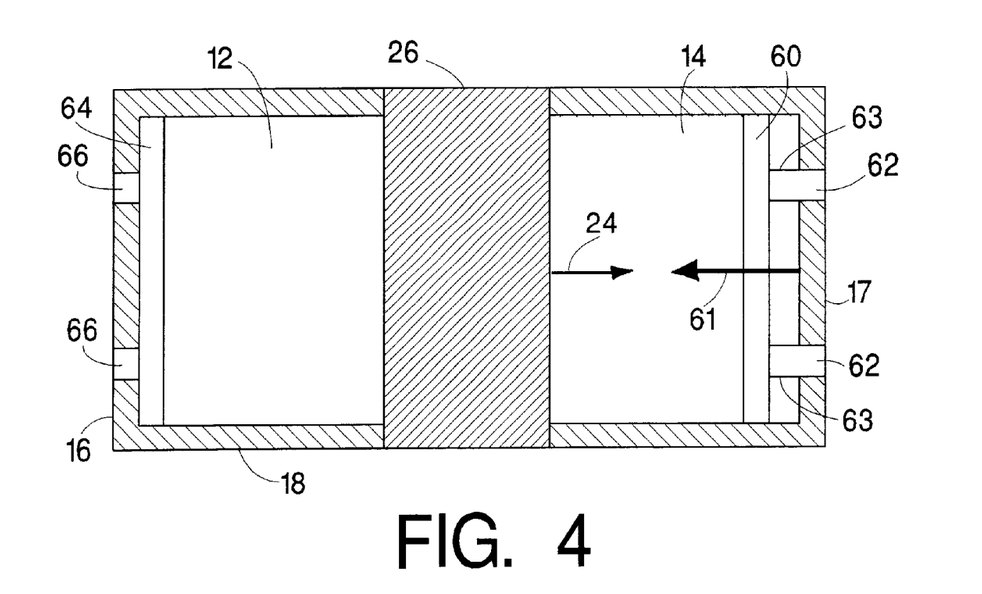
FIG. 4 is a schematic representation (top view) of a three-chambered assay device of the invention, in which a moveable wall is arranged to be advanced towards the delivery chamber.

As illustrated in FIG. 4, the new device can also include a moveable interior wall 60. The moveable wall can be made of plexiglass, glass, or other such rigid material. The wall can be included in one or both chambers 12 and 14. FIG. 4 illustrates the movement of wall 60 in test chamber 14. Wall 60 is advanced by two screws 62 in two holes 63 in the side wall 17 of the device. These screws can be made of, for example, plastic. The turning of the screws causes wall 60 to move towards delivery chamber 26 in the direction of arrow 61. Wall 60 is positioned with respect to the interior surfaces of the device and the screws so as to remain parallel to delivery chamber 26 as it is advanced. Movement of this wall increases the mechanical confinement pressure inside the test chamber 14. When test chamber 14 contains a gel, this movement creates a regional pressure gradient, specifically an increase in pressure in the area closest to moveable wall 60.

In the device illustrated in FIG. 4, wall 64, which is arranged not to move, is located at one end of the device. Wall 64 can be fixed to the side 16 of the device by fitting screws that do not permit an advancement of the wall to the interior of chamber 12. Alternatively, this chamber can completely lack a wall and holes 66 and instead be sealed by side wall 16 of the chamber. In another alternative, holes 66 can be fitted with screws similar to screws 62, which can be used to seal holes 66, or to move wall 64 towards delivery chamber 26.

Inserts for Assay Devices

Figure 5:
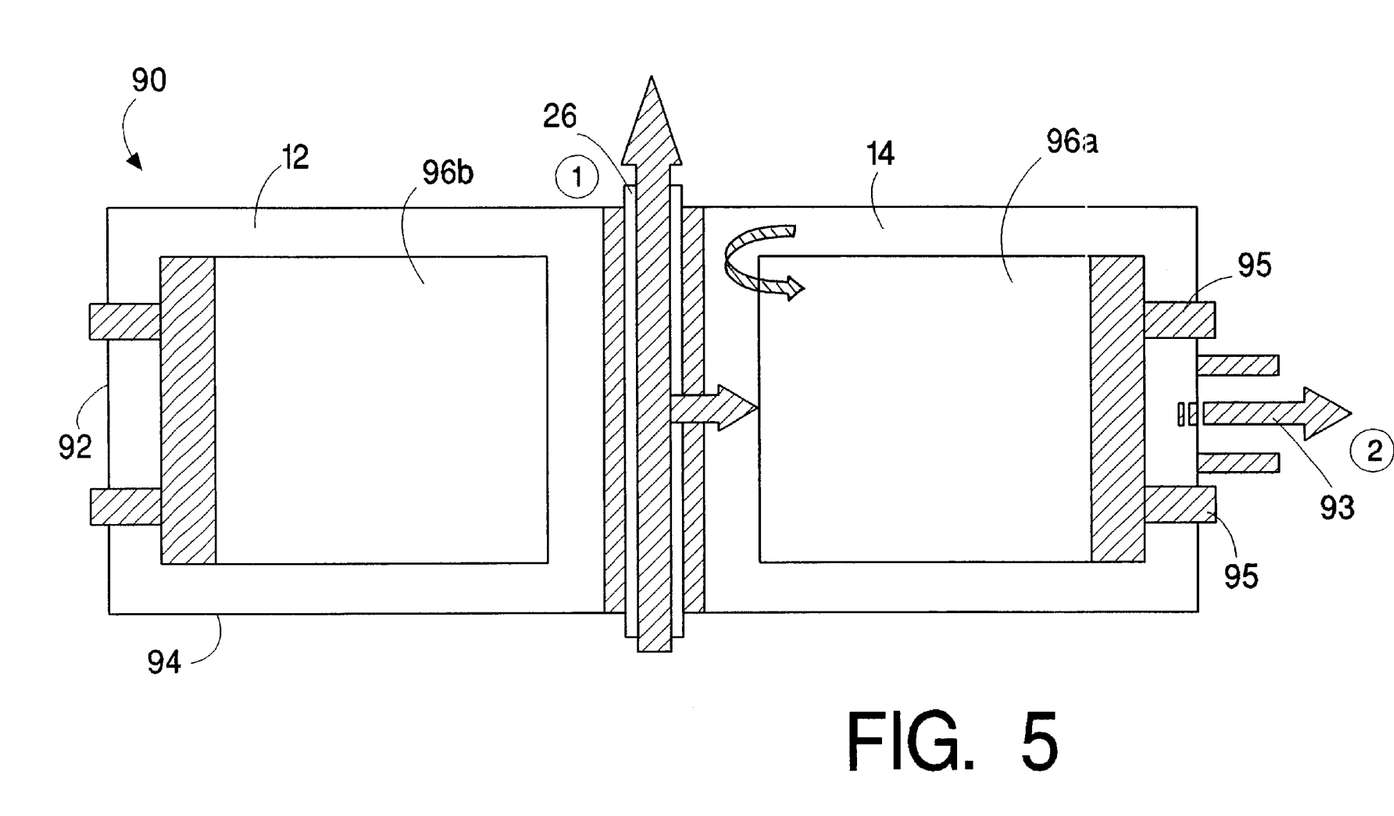
FIG. 5 is a schematic representation (top view) of a three-chambered assay device of the invention.

A top view of a device 90 of the invention is shown in FIG. 5. This device has a first side wall 92 and a second side wall 94. The walls of the device can be made of the rigid, transparent materials described herein, e.g., plexiglass. As in the device 10 depicted in FIG. 1, device 90 is divided into a test chamber 14, a control chamber 12, and a delivery chamber 26. The delivery chamber 26 is designed in the same manner as the delivery chamber of device of FIG. 1. Device 90 contains inserts 96a and 96b that can contain cells and a matrix. In FIG. 5, inserts 96a and 96b are placed in each of the test and the control chambers. Each of the inserts is surrounded by a layer of media on all sides when the device is used. A device can optionally be constructed and used containing an insert in only one chamber. In one example, the walls of the device are made of plexiglass and are 1 mm thick.

The use of an insert and insert holder, as described below, is particularly advantageous when removal of the cell/matrix mixture from the device is desired. Insert 96a functions as a removable container that holds cells and a matrix. In FIG. 5, insert 96a is depicted as a cube, though it can take any shape, e.g., rectangular, round, or elliptical. The insert contains at least one opening, e.g., a hole, to permit media to access the cells contained therein. For example, the insert can contain holes on one side, e.g., the side that faces a delivery chamber.

Figure 6A:
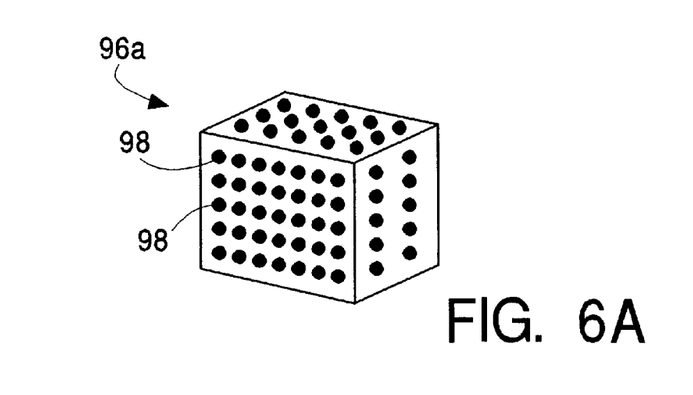
FIG. 6a is a schematic representation of an insert.

The cube-shaped insert 96a of FIG. 5 is depicted in more detail in FIG. 6a. The insert 96a has holes 98 on all six sides, to allow media to access the interior of the insert 96a from all sides. In some cases, an insert may have an opening only on one surface, e.g., a surface facing the flow from the delivery chamber. The insert 96a has holes 98 that preferably are not large enough to permit escape of the matrix and cellular material from the insert. In one embodiment, the insert 96a is a six-walled cube (4×4×4 mm) with plexiglass walls, e.g., 1 mm thick. In this embodiment, all six sides are perforated with holes (having a diameter of 0.1–0.3 mm), e.g., in a 1×1 mm grid. The insert can have a removable top, e.g., a sliding or drop down top, that facilitates the placement of cells into the insert and their removal therefrom. The insert is held in its x, y, z position in the chamber by bottom and top nodes, as described below.

Device 90 of FIG. 5 is designed so that the insert can be removed from a chamber, e.g., a test chamber, by sliding back the lid of the device to analyze cells contained within the insert. When removed from the chamber, the cells can be analyzed while in insert 96*a* or following their removal from the insert. When analyzing the cells while in the insert, e.g., to perform online image analysis, the insert may optionally be placed in an insert holder. The insert holder functions to contain the insert when removed from the device, while minimizing the rate at which the gel dries, e.g., a surface of the insert holder covers one or more of the openings of the insert. The insert holder is preferably manufactures with a transparent material, e.g., plexiglass or glass, as described herein. For example, when a cube-shaped insert is used, the insert holder can be four sided, with a removable top and/or bottom. The insert holder, with the insert contained therein, can then be subjected to various analyses, e.g., laser scanning confocal microscopy, or light microscopy.

In those devices that use an insert, a moveable wall can be placed within the insert to achieve the advantages described herein conferred by such a wall. For example, a moveable wall of an insert can be operated by using screws that extend from outside the device, through the external wall, through the media in the chamber, and through a wall of the insert. As shown in FIG. 5, the screws 95, when turned, push on the moveable wall and increase the pressure gradient within the interior of insert 96*a*.

If a moveable wall is not needed for a particular experiment, insert 96*a* can be sealed, e.g., using the short screws as described therein. The device can be closed using a similar mechanism. If the moveable walls of an insert have been used, e.g., advanced within the insert, then the screws can be loosened to allow for removal of the insert from the chamber. The chamber walls can then be sealed, e.g., with 1 mm plugs. The screws can be placed back into the insert after its removal from the chamber.

Figure 6B:
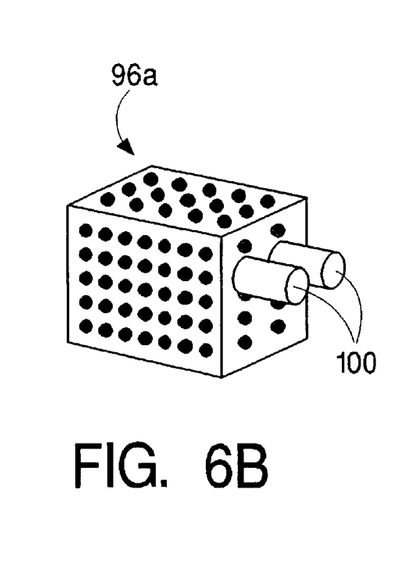
FIG. 6b is a schematic representation of an insert with two screws positioned on one side of the insert.
Figure 6C:
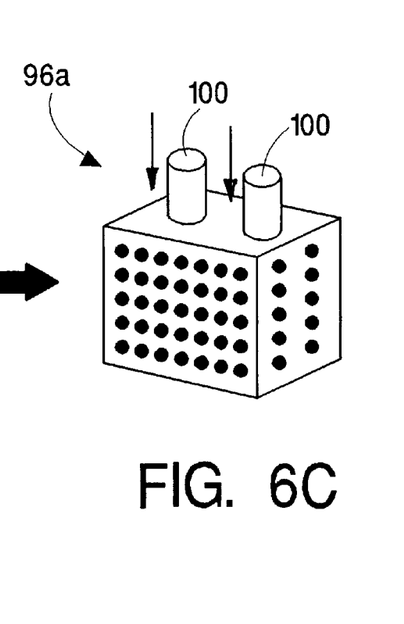
FIG. 6c is a schematic representation of the insert of FIG. 6b rotated 90 degrees.
Figure 6D:
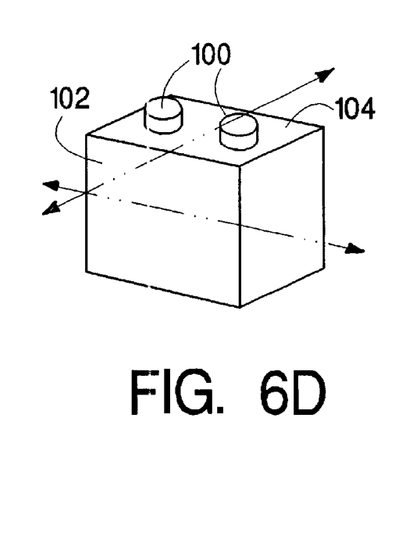
FIG. 6d is a schematic representation of an insert within an insert holder.

FIGS. 6*b*, 6*c*, and 6*d* depict an example of devices and methods for the handling of an insert with a moveable wall, following the removal of the insert from a chamber. In FIG. 6*b*, screws 100 are repositioned in the insert 96*a* following the removal of insert 96*a* from the chamber. In FIG. 6*c*, the insert is turned 90 degrees with respect to FIG. 6*b*. A scale can be added to the insert, e.g., to the sliding lid of the insert, e.g., by laser scratching. This scale can be used as a marker to ensure that the moveable wall is at the same location when the screws are repositioned as it was while the insert was in the chamber. If the moveable wall has changed position during the process of removing the insert, then the wall can be returned to its proper position as indicated by the scale. Following the rotation of the insert in FIG. 6*c*, the insert can be placed in an insert holder 102, as depicted in FIG. 6*d*. The insert holder 102 of FIG. 6*d* is a four sided device, with a removable top 104 and a removable bottom. The removable top 104 is a drop down top that fits around the screws 100, so that the screws need not be removed from the insert for the placement of the top. Following an analysis of the material within the insert, the insert can be pushed through the sliding bottom of the insert holder and placed back in the test chamber (by removing and repositioning the screws in the reverse order of the steps described above).

Figure 3B:
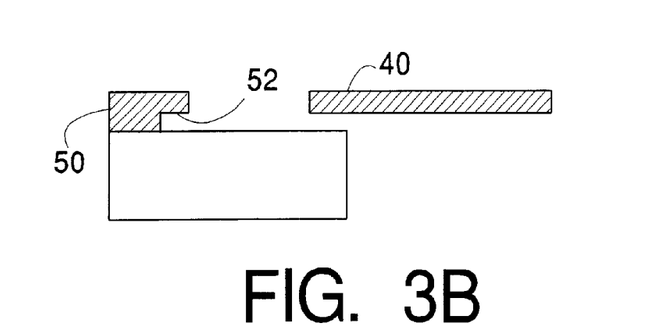
FIG. 3b is a schematic representation (side view) of an assay device of the invention, in which the cover is removed and the ridge for attachment of the cover is visible.
Figure 7:
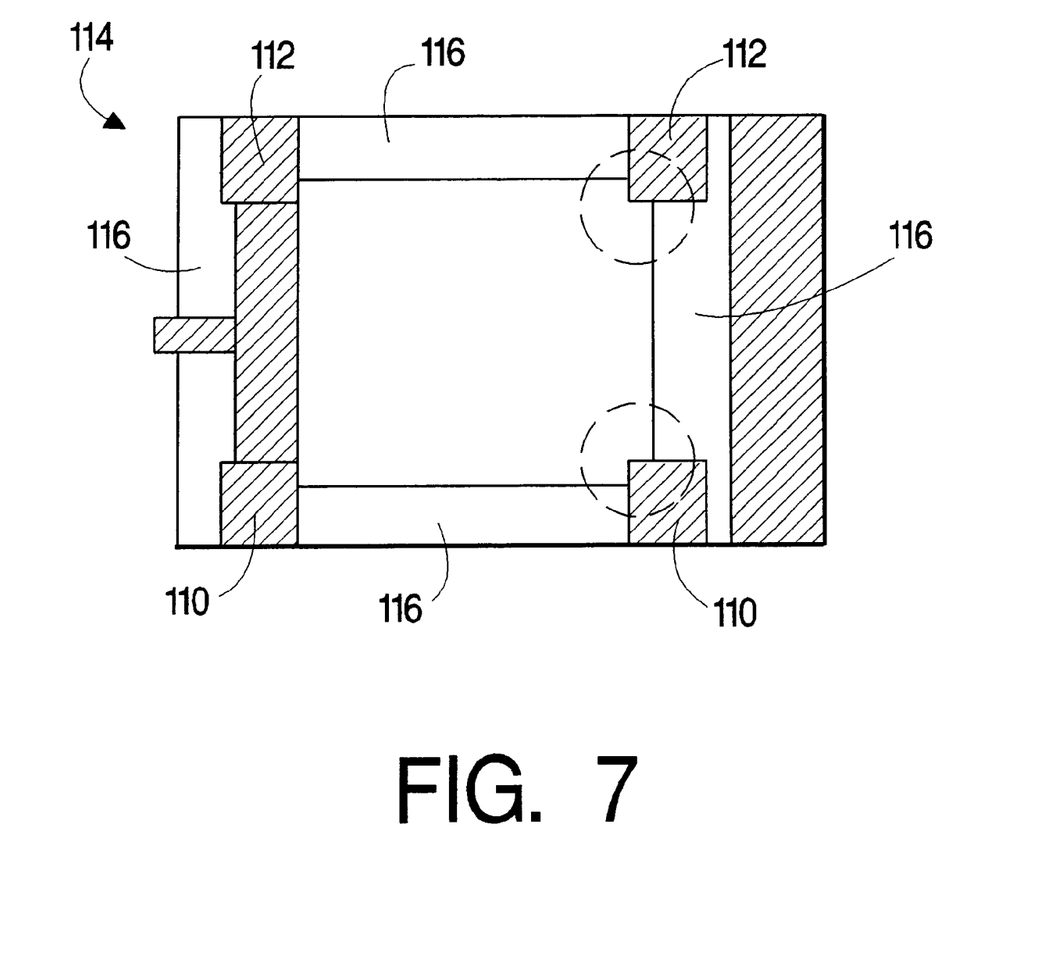
FIG. 7 is a schematic representation (side view) of a chamber of a device of the invention containing an insert.

A device can contain a node or nodes that prevent an insert from moving within a chamber. Nodes can be designed to permit media to access all of the sides of the insert. In device 114 depicted in FIG. 7, bottom nodes 110 are affixed to the bottom of the chamber. Media 116 surrounds the insert on all sides. Top nodes 112 are affixed to the top corner of the insert 96. In this embodiment, the lid for the device is a slidable lid that glides over the entire top of the device to make a seal. As depicted in FIG. 3*b*, the lid slides over both chambers, and additionally rests on the top nodes 112 of the insert 96. Nodes can be placed on the lid, if the device is designed such that the nodes do not interfere with the attachment of the lid to the device.

Chamber Outflow

A device of the invention can include a chamber outflow mechanism. An outflow can be incorporated into a test chamber, a control chamber, or both. The device 90 of FIG. 5 contains a test chamber outflow 93. The diameter of the outflow can be of the same size, smaller, or larger than the diameter of the removable connectors on the ends to the central chamber. When used in combination with an insert in a device, the outflow permits the continuous flow of media into a chamber, around the cells in the insert, and out of the chamber. The outflow can optionally be connected to a continuous pump system, as described below.

Connecting the Device to a Pumping System

Figure 8:
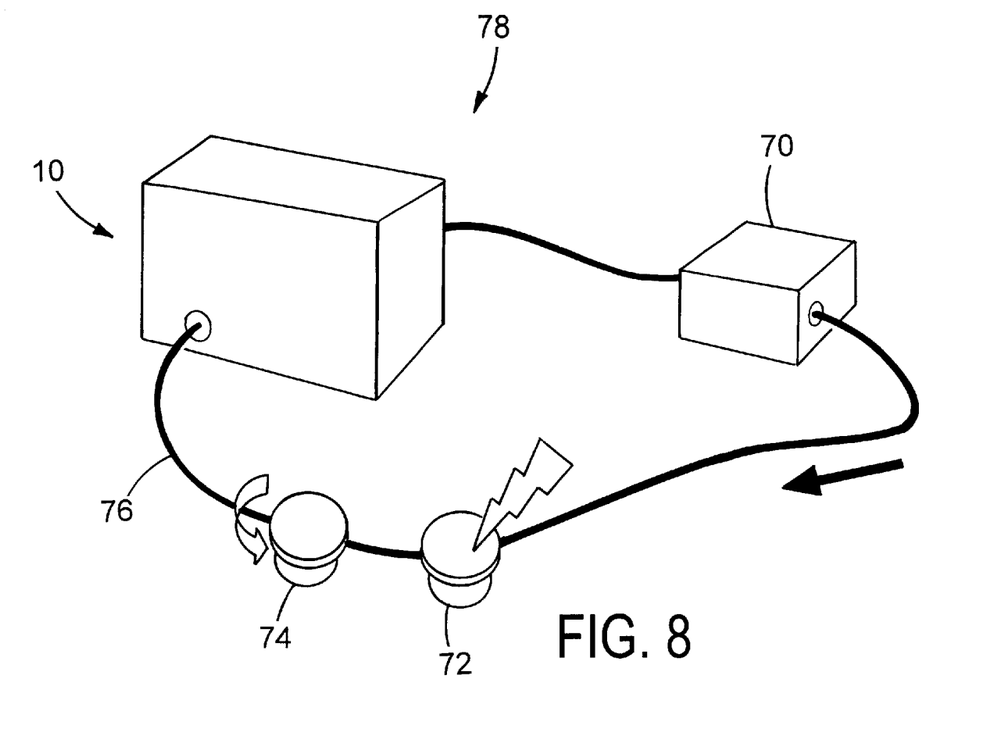
FIG. 8 is a schematic representation of a single pump assay system of the invention.
Figure 9:
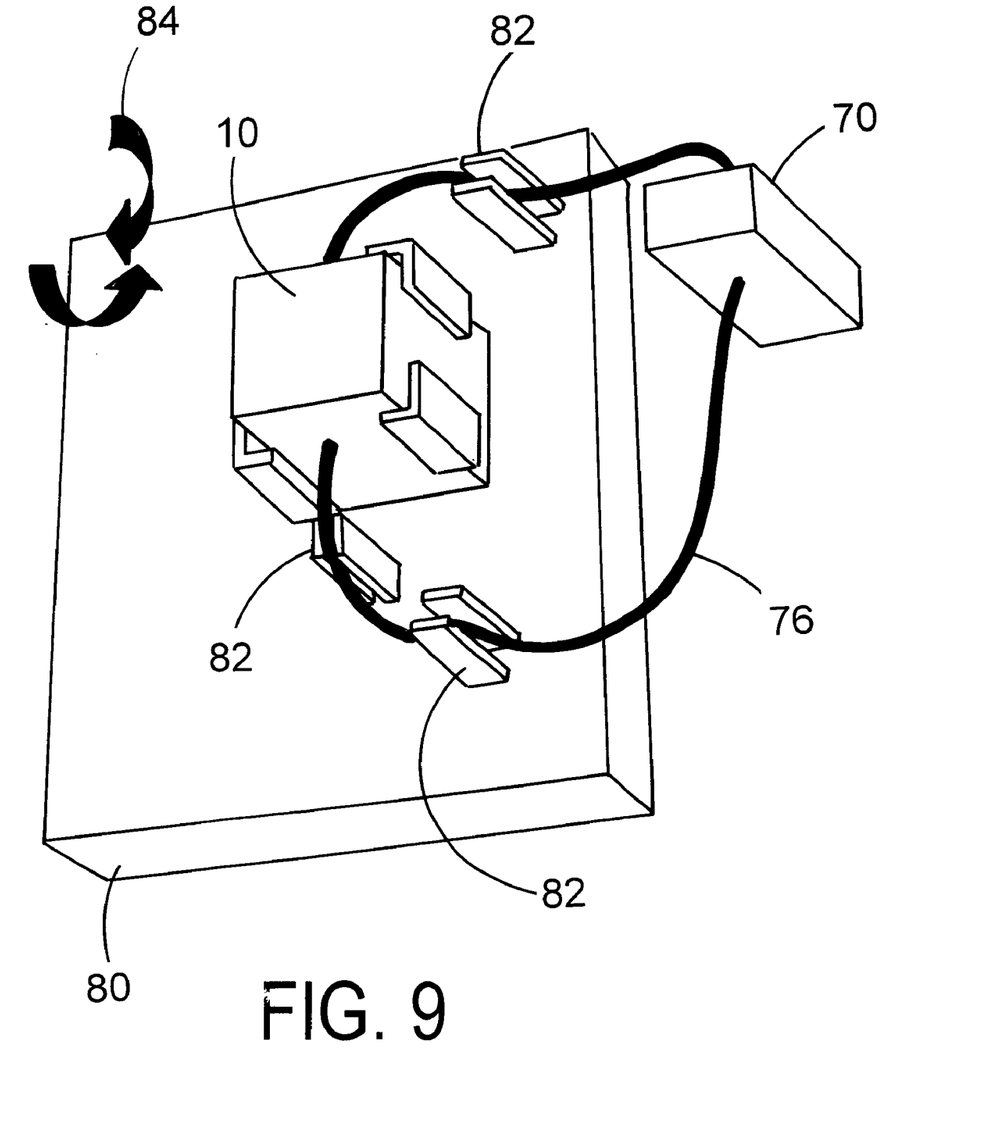
FIG. 9 is a schematic representation of an assay system of the invention attached to a flexible table.

As illustrated in FIG. 8, devices 10 and 90 can be attached to a pump 70, e.g., a continuous peristaltic pump, via conduits, e.g., tubing, 76. A switch 74 can also be used in the assay system 78. The peristaltic pump 70 can be a low flow pump, having a flow rate of 0.03–8.2 ml/min (Fisher). Alternative pumps that can be used in the invention include an ultra low flow pump (0.005–0.9 ml/min) and a medium flow pump (4.0–85.0 ml/min). Peristaltic pump 70 creates a continuous flow that can be varied as desired to permit the delivery of fluid and or gas to test chamber 14. As shown in FIG. 9, the assay system 78 can be placed on a table 80 that can be rotated 84 as desired, e.g., if flexible/rotating links in the tubing prevents twists. Clamps 82 keep the conduits 76 in place regardless of the angle of the table 80. Any leakage in the system can be measured, e.g., by the use of fluorescent spheres (for example, 1–2 $\mu$m in size). The entire assay system 78, including the peristaltic pump 70, can be placed inside an incubator and/or placed next to a microscope. A direct AC-adapter can be used for the pumps of the assay system. Alternatively, a battery, e.g., a 9 or 12 volt battery, can be used in the pump 70.

Figure 10:
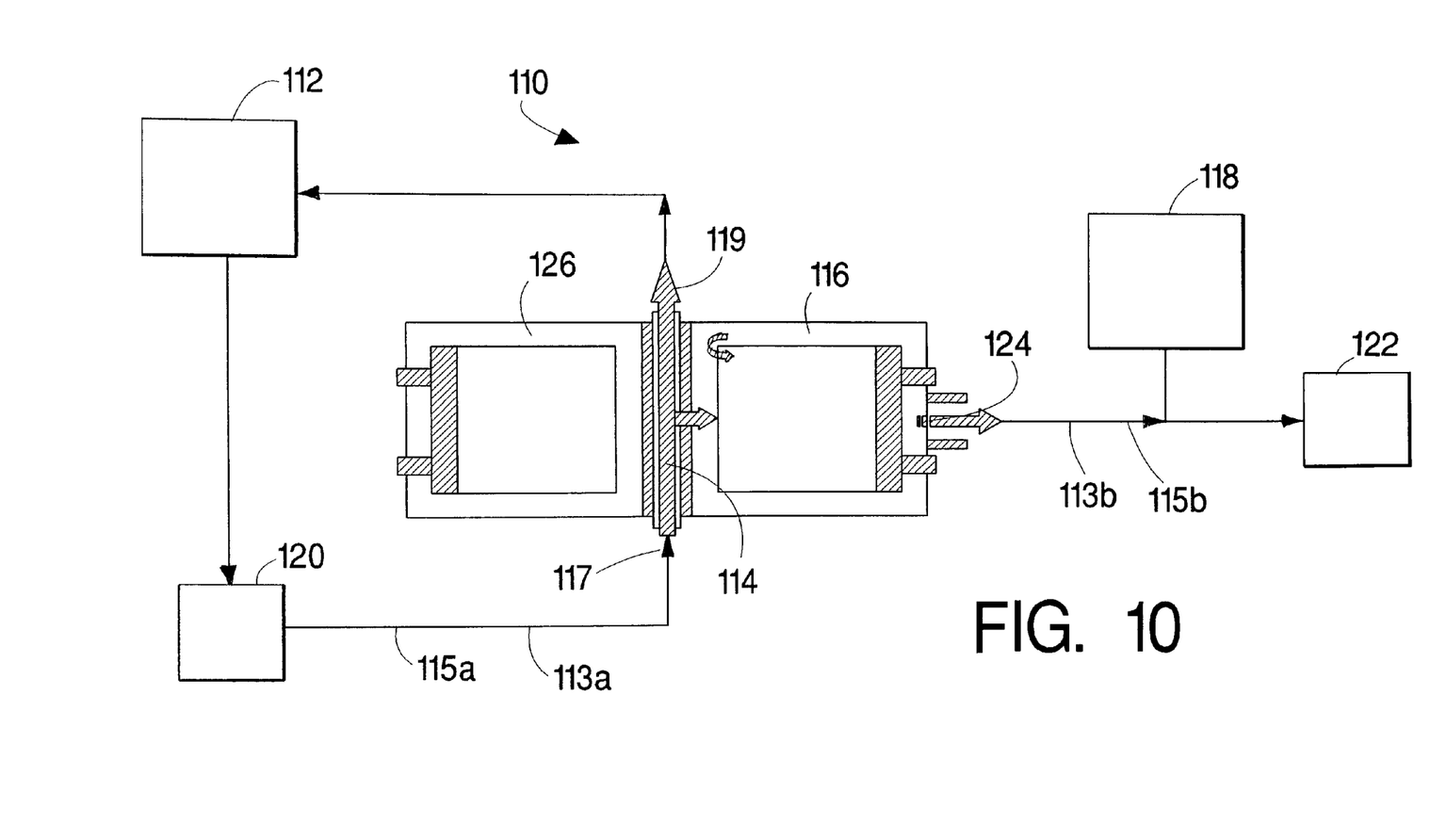
FIG. 10 is a schematic representation of a dual pump assay system of the invention.

In FIG. 10, a device 110 is attached to two peristaltic pump systems. Pump 112 circulates media through the delivery chamber 114 and into the test chamber 116. Pump 118 effects the outflow of media (and optionally waste products) from the test chamber 116. In this system, reservoirs are used for continuous supply (reservoir 120) and continuous removal (reservoir 122). The reservoirs can be equipped with filters, e.g., to avoid vacuum and contamination. The system can be constructed, and the pumps can be adjusted, so that the outflow velocity of the test chamber is higher, lower, or equal to the inflow velocity. Although FIG. 10 depicts a non-continuous two pump system, a continuous system is also included within the invention.

Measurements of the fluid content of the outflow 124 can provide information as to metabolism within the cell system in test chamber 116. In addition, the flow in the device 110 can be reversed to expose cells, e.g., cells in the test chamber 116, to conditioned medium. The flow from pump 112 and/or pump 118 can be reversed. Measurements of metabolites can also be conducted in the control chamber 126, e.g., in the same manner as for the test chamber 116 or by microsampling through the threads which hold the wall-operating screws.

Because the chamber can be constructed to lack air holes, it may not be necessary to place the system 78 inside of a $CO_2$ incubator. Rather it may be necessary to only ensure that device 10 remains heated as is required for maintenance of the cells therein. Therefore, system 78 can be potentially operated outside of an incubator in an environment that warms device 10. For example, the device 10 can be placed inside of a heated plexiglass chamber that contains either the entire system 78 or that contains only the device 10 and has holes in the sides of the plexiglass that allow the conduits to enter and exit the chamber and connect with the pump. The main requirement is that the medium or other liquid or gas that is pumped by the pump 70 reaches appropriate culturing temperatures by the time it enters delivery chamber 26.

Nonetheless, for long-term experiments the entire device can be placed in an AC-equipped incubator, thus operating both pump-systems from inside. The battery mechanism allows the continuation of the flow while taking images.

A device described herein can be constructed to measure and/or adjust gas, e.g., $O_2$ and/or $CO_2$, concentrations within the device. For example, the system depicted in FIG. 10 can include a measurement device 113a for pump system 112 and a measurement device 113b for pump system 118. A measurement device can be included in one or both of the pump systems. In one embodiment, the measurement device detects the $CO_2$ concentration and communicates with another device to ensure that the concentration is maintained within an appropriate range, e.g. about 5% $CO_2$. The use of such measurement and/or adjustment devices allows for the construction and operation of an autonomous device, e.g., one that does not require a specific atmosphere for the operation of the device. Devices containing measurement and/or adjustment devices are particularly useful for long term cultures, e.g., those that use the inserts described herein.

In the system 110 depicted in FIG. 10, the measurement device 113a is located between the reservoir 120 and the inflow 117, but after the switch 115a. Likewise, the measurement device 113b is located between the reservoir 120 and the outflow 124, but before the switch 115b, e.g., to allow measurements to be taken before samples are withdrawn from the system.

The substances that can be pumped through the assay system 78 include, for example, liquids (solutions or dispersions) such as medium (enriched or deprived), growth factors, growth inhibitors, chemotherapeutic substances, radiosensitizers, and prodrugs as required for various gene therapy experiments, as well as gases, such as oxygen, carbon dioxide, and mixtures of gases. The substances can be added to the system via the injection port 72. In addition to the injection port 72, plugs or screws 62 (FIG. 4) can also be removed from holes 63 to supply substances directly to the matrix inside test chamber 14 or into the insert 96 or the medium around the insert. Specifically, Hamilton microsyringes as well as micropipettes can be used to deliver agents into the gel through holes 63. These agents can include viral vectors, material for microinjection, dye to study cell communication, or substances to generate competing growth factor loci. Delivery of agents via the holes 63 differs from delivery via holes 22a and 26a in the delivery chamber 26 in that it permits delivery to a different site in the tumor as well as the delivery of solid components. The holes 22a and 26a in the delivery chamber are particularly well-suited to the delivery of liquids, whereas the holes 63 permit the introduction of solid substances, for example by mixing the solid in a gel and injecting it through hole 63. Furthermore, delivery of a substance via a hole 63 permits the use of fine techniques such as the microinjection of single cells within the test chamber 14.

Culturing Cells in the Assay System

Both primary cells and established cell lines can be assayed using this system. Both tumor and non-tumor cells can be used. For example, tumor cells, endothelial cells, stem cells, and a variety of tissue specimens and co-cultures can be propagated in the devices of the invention. The cells to be studied can optionally be cultured in vitro prior to being placed in the assay device. Standard media and incubation conditions can be used.

It is expected that a variety of tumor cells can be tested in the assay. These include various brain tumors, breast tumors and lung tumors. Preferably, tumor cell spheroids are collected to be used in the device. Many glioma and non-glioma cell lines form spheroids, and both spinner flask methods as well as agarose medium superlayer methods enable the formation of spheroids from cell suspensions.

Spheroids can be washed to remove serum and then placed in a gel, such as Matrigel® (BIOCAT®, Becton Dickinson, Franklin Lakes, N.J.). Although the composition of the gel is important (e.g., the gel consistency permits tumor cells to proliferate and invade the gel matrix), it need not necessarily be growth factor-reduced Matrigel®. The gel can be mixed with medium at a ratio of 3:1 (gel:medium). The medium to be used can vary widely. For example OPTI-MEM® or DMEM can be used with various concentrations of growth factors. Survival time of the spheroids can be extended by adding higher growth factor concentrations or by adding full (serum supplemented) DMEM. Similarly, if using an insert, the medium composition in the circulation can be altered to influence the viability of the cells within the insert.

If not using an insert, and its associated exposure to a continuous replenishment of nutrients, then experiments are typically stopped at about 144 hours after inserting the multicellular tumor spheroid into the device to diminish the effects of central multicellular tumor spheroid-quiescence and necrosis. This marks the time-point at which volumetric growth increase typically becomes insignificant. However, successful experiments have been performed in which cells were kept alive for more than 168 hours by using "full" or complete medium for the gel composition. The experimental setting can therefore be tailored to a specific cell line, a specific commercially available or custom-made gel, or a specific time frame. Furthermore, variations in either gel composition or gel consistency enable the investigation of the dependence of growth patterns on environmental conditions. By using an insert, the time frame will be significantly extended as a continuous supply of nutrients through the pump systems allows for longer in vitro cell growth periods.

The effect of various substances on cell growth can be evaluated by providing the substance either in the original gel matrix, adding the substance via one of the holes 63 of the device into the gel or, if an insert is used then also into the medium of the chamber, or by pumping the substance through the cylinder in the delivery chamber and allowing it to enter the test chamber 14 by way of holes 22a and 26a. Any substance that can enter the system through one of these mechanisms can be tested with respect to its impact on the system. These substances include, for example, growth factors and anti-cancer therapeutics. The outflow reservoir 122 can be used to determine the metabolic impact of these substances on the cell system.

Radiation studies, such as Boron Neutron Capture Therapy (BCNT), can also be performed on cells, e.g., tumor cells, in the assay system. BCNT entails the irradiation of boron-10 ($^{10}B$), a non-radioactive stable isotope with low-energy thermal neutrons, in order to yield high linear energy transfer particles $^4He$ and recoiling $^7Li$. Since it is preferred for BCNT to localize a high number of $^{10}B$ atoms on or within the neoplastic cells, growth factors can be tagged with $^{10}B$. For example, a limited amount of growth factors (e.g., 50–100 ng/ml EGF/TGF-α) can be implanted or injected to effect a regional impact on the invasive system. Growth factor-loaded agarose-gel particles can be used in the assay. Similarly, $^{10}B$ can be injected locally within the assay to evaluate its selective cell killing ability. Furthermore, growth factors and $^{10}B$ can be co-implanted or co-injected at the same site in a combined approach. The growth factors and $^{10}B$ can also be incorporated in polymer platelets by applying technology currently used for drug-wafers.

Analysis of Cell Growth in the Assay Device

The new assays are designed to permit the study of cells, e.g., tumors as complex, dynamic, self-organizing biosystems, i.e., the study of the adaptive interdependency of these key features. The interdisciplinary approach includes tumor biology, bioengineering, mathematical biology, physics, materials science, computational science, and complex systems science. The approach is directed to ultimately develop an array of computational models based on experimental data. To gain those data sets, one needs to develop novel experimental settings, preferentially only one, that are capable of describing tumors as multi-featured systems.

After the culture period in the device has been completed, the entire gel cube can be fixed and preserved for histological analysis. Specifically, formalin is added to the chamber, the whole gel is fixed, and a cube with the cell, e.g., a tumor cell, in place or an insert is extracted from the chamber. This entire coe is embedded in paraffin and can then be divided into microsections. Classical pathological evaluations can be performed on the sections, including immunohistochemistry, DNA analysis (both genetic and epigenetic), and advanced Laser Capture Micro-Dissection (LCM), all using standard techniques, to search for regional genetic and epigenetic changes.

Proliferation of cells in the device can be measured by various techniques. For example, cells taken from the device can be digested with trypsin to make a single cell suspension and then counted (e.g., using a Coulter Counter) to determine the extent of proliferation that has occurred since the start of the assay. Additionally, a morphometric measurement can be taken that measures the volume of a cell mass as a means to calculate the total cell number.

Invasiveness of cells in the device can be measured by various techniques, such as statistical and fractal analysis, mathematical and computational methods combined with advanced imaging analysis, as well as histological methods.

Cells can also be extracted from the gel for further growth either during the culturing period or at the end of the culturing in the assay device. The reculturing of cells that have been extracted from the device allows for their expansion to further characterize various cell types of interest. Cells can be re-cultured using a specific gel-digesting enzyme such as Dispase or MatriSperse (BIOCAT/Becton Dickinson). This enables the analysis and or expansion of sub-populations from different regions of the biosystem.

Cells within the device can also be examined as the assay is in progress for 3D analysis over time, without unhooking the device from the continuous pump. For example, light microcopy can be used to take photographs of tumor cells. The size and mobility of the table upon which the device rests allows it to fit under most microscopes. Photographs can be taken at time intervals and can be taken at specific positions in the device by returning the microscope to a designated location. Video time-lapse microscopy can also be performed, optionally using a laser to scratch an x, y, z grid on a surface of the device that allows the use of coordinates on the device itself (rather than coordinates on a microscope) to find and examine specific locations, and therefore obviates the need to use the same microscope for all measurements.

Fluorescent techniques can also be used to evaluate cell growth. The cells can be prestained with a fluorescent substance before being placed inside the gel. Confocal laser scanning microscopy can then be used to analyze the cells in a three-dimensional setting. Some of the fluorescence intensity can be lost in this system as a result of dilution of the fluorescent substance by cell division and by bleaching. However, in some circumstances the fluorescent substance can be replenished by its addition to the assay system while the assay is in progress using the routes described earlier. Alternatively, the cells can be genetically engineered before or during the assay to express a gene encoding a fluorescent product, such as green fluorescent protein (GFP) or red fluorescent protein (RFP). The gene encoding a fluorescent product can be delivered to a cell for example by a retroviral vector, which can be added later when an experiment is in progress, e.g., using the routes described earlier.

Advanced imaging techniques can also be used to analyze cells with in the device. The assay fits the needs for microstructural analysis of the gel with microtomography, microMRI, and/or a Synchrotron. These techniques permit the analysis of any voids and solid structures within the gel. This analysis is important to study the mechanisms of cell invasion such as the principle of "least resistance, most permission and highest attraction."

The insert holder allows these image-analyses of the cell-gel composition even when the insert is used. In that case, the placement of the insert into the insert holder can reduce the thickness of the material which has to be imaged as compared to image the insert within the chamber.

EXAMPLES

The invention will be further described in the following examples, which do not limit the scope of the invention described in the claims.

Example 1

Culture of the Human U87MGmEGFR Glioblastoma Multiforme Cell Line as a Spheroid

The human U87MGmEGFR glioblastoma multiforme cell line was cultured in DMEM (GIBCO BRL, Life Technologies™, Grand Island, N.Y.) supplemented with 10% heat inactivated cosmic bovine serum (HyClone®, Logan, Utah) and 400 µg/ml in G418 (Life Technologies™) in a humidified atmosphere of 5% $CO_2$ at 37° C. Compared to the wild-type epidermal growth factor receptor (wtEGF-R), these stable-transfected cells co-express also an EGFR variant (mEGFR=ΔEGFR, $EGFR_{vIII}$, ($2 \times 10^6$/cell)). This specific mEGFR has an in-frame deletion of 801 bp of the coding sequence for the external ligand-binding domain, rendering the receptor constitutively active and incapable of signal-attenuation by downregulation. This genetic rearrangement is rather common in glioblastoma multiforme tumors and in vitro the mutation confers enhanced tumorigenicity by increasing proliferation and reducing apoptosis. Due to a yet unknown mechanism U87MGmEGFR cells rapidly form multicellular tumor spheroids (MTS) in culture after reaching monolayer confluency and detach at a certain size due to the laminar flow dynamics of the surrounding medium.

The floating U87MGmEGFR MTS were collected with Pasteur-pipettes and washed gently in OPTI-MEM® (GIBCO BRL) to eliminate residual serum. Using Pasteur-pipettes the spheroids (≈500–700 µm in diameter, (0.7–1.0× $10^4$ U87MGmEGFR cells)) were then placed in between two layers of growth factor-reduced matrix, Matrigel® (GFR-M) (BIOCAT®, Becton Dickinson, Franklin Lakes, N.J.), which forms a reconstituted basement membrane at room temperature. Initially extracted from the Engelbreth-Holm-Swarm mouse tumor, this specific matrix variant contains less than 0.5 ng/ml EGF and 1.7 ng/ml TGF-β (as well as 61% laminin and 30% collagen IV) as compared to the commonly used full-Matrigel. We then reduced these growth factors and extracellular matrix (ECM) proteins even further by supplementing the gel with reduced serum medium OPTI-MEM® at a ratio of 3:1 GFR-M to medium. This assay was performed in a completely enclosed 1 cm$^3$ plexiglass cube, having no input/output connections or openings to a delivery chamber. The total GFR-M/OPTI-MEM® volume per well of the 1 cm$^3$ device was about 2 ml per chamber. To diminish the effects of central multicellular tumor spheroid quiescence and necrosis, the experiments were stopped after 144 hours post multicellular tumor spheroid placement. This marks the time-point when the volumetric growth increase becomes insignificant. The one-day change in volume drops below 15%, which equals less than half the values obtained during the steep growth phase (≈30% between 48 and 96 hours), and therefore signals the onset of the decelerating growth phase.

Example 2
Invasive Network Developing in the Three-Dimensional Assay

The human U87MGmEGFR glioblastoma multiforme cell line was cultured in a 1 cm$^3$ plexiglass cube device as described in Example 1, except that DMEM full medium (serum supplemented) was used. This enriched medium allows for an extended growth of the cells in the assay. The multicellular tumor spheroid (U87MGmEGFR) was analyzed at time 24 hours and at time 120 hours. The invasive cells were seen to extend the initially established branches. A darkened structure, an attractor-tube, was detected which consists of a nutritive gel with a high consistency. The lack of invasive branches toward this side along with the sustained volumetric expansion of the attached multicellular tumor spheroid demonstrated the impact of this solid attractor on the tumor system. By avoiding a higher consistency structure, the expanding invasive branches appear to follow the proposed principle of "least resistance and most permission."

Other Embodiments

It is to be understood that, while the invention has been described in conjunction with the detailed description thereof, the foregoing description is intended to illustrate and not limit the scope of the invention. Other aspects, advantages, and modifications of the invention are within the scope of the claims set forth below.

What is claimed is:

1. An assay device for measuring the proliferation, invasion, or proliferation and invasion of cells, the device comprising:
   a test chamber;
   a first delivery chamber arranged to contact the test chamber;
   the first delivery chamber comprising a wall with an opening to enable fluid communication between the first delivery chamber and the test chamber; and
   a hollow cylinder enclosing a lumen and arranged within the first delivery chamber, the cylinder comprising a wall with a hole that can be aligned with the opening in the first delivery chamber wall to enable fluid communication between the cylinder lumen and the test chamber, wherein the cylinder comprises an inflow opening at one end that permits flow of fluid into the cylinder and an outflow opening at a second end of the cylinder that permits flow of fluid out of the cylinder.

2. The assay device of claim 1, further comprising a control chamber arranged to contact the first delivery chamber.

3. The assay device of claim 1, further comprising a cover that sealingly contacts the delivery chamber and the test chamber.

4. The assay device of claim 1, further comprising a first moveable interior wall that is arranged to move within the test chamber.

5. The assay device of claim 1, further comprising a plurality of cylinders, each having a hole that can be aligned with the opening in the delivery chamber wall to enable fluid communication between the cylinder and the test chamber, wherein the cylinders each have a hole of a different size.

6. The assay device of claim 1, further comprising a second delivery chamber and a control chamber, wherein the second delivery chamber is arranged to contact the first delivery chamber and the control chamber is arranged to contact the second delivery chamber.

7. The assay device of claim 6, further comprising a second moveable interior wall that is arranged to move within the control chamber.

8. The assay device of claim 1, wherein the test chamber comprises an outer wall with an opening to enable fluid communication between the test chamber and the exterior of the assay device.

9. The assay device of claim 1, further comprising a hollow insert constructed to fit within the test chamber.

10. The assay device of claim 9, further comprising a moveable interior wall that is arranged to move within the insert.

11. An assay system for measuring the proliferation, invasion, or proliferation and invasion of cells, the system comprising:
    the device of claim 1;
    a pump having an input and an output;
    a first conduit that connects one end of the hollow cylinder to the pump input; and
    a second conduit that connects a second end of the hollow cylinder to the pump output to permit flow of fluid from the pump, through the cylinder in the delivery chamber of the device, and back to the pump.

12. The assay system of claim 11, further comprising an injection port connected to the first or second conduit that permits the introduction of substances into the system.

13. The assay system of claim 11, wherein the device further comprises a first moveable interior wall that is arranged to move within the test chamber.

14. The assay system of claim 13, further comprising a control chamber arranged to contact the first delivery chamber.

15. The assay system of claim 14, further comprising a second moveable interior wall that is arranged to move within the control chamber.

16. The assay system of claim 11, wherein the test chamber comprises an outer wall with an opening to enable fluid communication between the test chamber and the exterior of the assay device.

17. The assay system of claim 11, further comprising a hollow insert constructed to fit within the test chamber.

18. The assay system of claim 17, further comprising a moveable interior wall that is arranged to move within the insert.

* * * * *